United States Patent
Ehrlich

(10) Patent No.: US 11,497,909 B2
(45) Date of Patent: Nov. 15, 2022

(54) REMOTE PAIN MANAGEMENT THROUGH ELECTRICAL STIMULATION OF MERIDIAN BODY LINES

(71) Applicant: Steven Ehrlich, Phoenix, AZ (US)

(72) Inventor: Steven Ehrlich, Phoenix, AZ (US)

( * ) Notice: Subject to any disclaimer, the term of this patent is extended or adjusted under 35 U.S.C. 154(b) by 365 days.

(21) Appl. No.: 16/751,614

(22) Filed: Jan. 24, 2020

(65) Prior Publication Data
US 2021/0228875 A1  Jul. 29, 2021

(51) Int. Cl.
*A61N 1/36* (2006.01)
*A61N 1/04* (2006.01)

(52) U.S. Cl.
CPC ....... *A61N 1/36021* (2013.01); *A61N 1/0476* (2013.01); *A61N 1/3603* (2017.08)

(58) Field of Classification Search
CPC ............ A61N 1/36021; A61N 1/36071; A61N 1/3603; A61N 1/476; A61N 1/456
See application file for complete search history.

(56) References Cited

U.S. PATENT DOCUMENTS

| 8,050,776 | B2 | 11/2011 | Shah |  |
| 2009/0281596 | A1* | 11/2009 | King | A61N 1/36182 607/46 |
| 2019/0001129 | A1* | 1/2019 | Rosenbluth | A61N 1/08 |

FOREIGN PATENT DOCUMENTS

| CN | 104146860 A | 11/2014 |
| CN | 107998504 A | 5/2018 |
| CN | 108853727 A | 11/2018 |
| CN | 109589494 A | 4/2019 |
| KR | 1020180086827 | 8/2018 |

OTHER PUBLICATIONS

1byone Products Inc., "Electronic TENS Therapy Pain Relief Kit, Instruction Manual," PL-029K8B Version 1.0, 7 pages.
Blue TENS Therapy Muscle, 3 pages.
Reliefband®|Motion Sickness Relief!, https://www.reliefband.com/pages/relief-band-special-1?utm_source=facebook&utm_medium=video&utm_campaign=rt&utm_term=acn&utm_content=swna, 8 pages.

\* cited by examiner

*Primary Examiner* — Alyssa M Alter
(74) *Attorney, Agent, or Firm* — Kinney & Lange, P. A.

(57) ABSTRACT

Aspects of the invention include a computer-implemented method requiring loading, via a processor, a meridian tool into an electrical device having an input screen. The method causes, via the processor, the meridian tool to display a human body image on the input screen. The method receives, via the processor, input signals from the input screen to indicate pain points on the human body image and displays, via the processor, a pain level input display on the input screen. The method receives, via the processor, pain level input from the pain level input display screen and causes, via the processor, the electrical device to provide controlling electrical pulses to a meridian acupuncture sleeve, wherein the controlling electrical pulses controls the application of current being applied to electrical pads within the meridian acupuncture sleeve to provide pain relief for the pain points on the human body.

17 Claims, 10 Drawing Sheets

1 = Pericardium Meridian
2 = Lung Meridian
3 = Heart Meridian

Anterior View

Anterior View

Posterior View

Proximal View

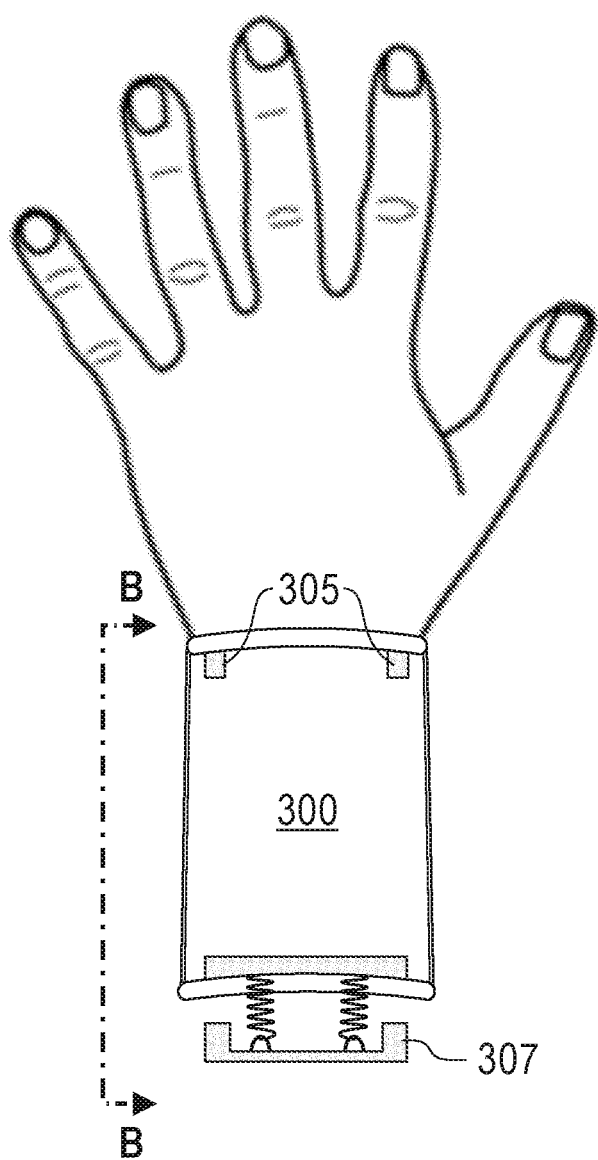
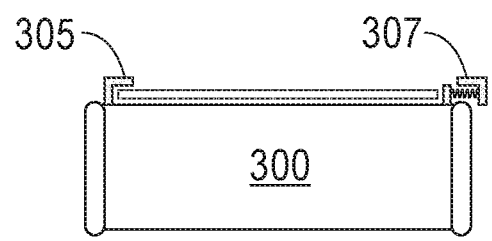
FIG. 3A
Posterior View
FIG. 3B

Anterior/Palmer View

4 = San Jao or Triple Burner Meridian

Posterior View

5 = Large Intestine Meridian

Side View/Lateral

6 = Small Intestine Meridian

Side View/Medial

1 = Pericardium Meridian
2 = Lung Meridian
3 = Heart Meridian

Anterior View

Anterior View

REMOTE PAIN MANAGEMENT THROUGH ELECTRICAL STIMULATION OF MERIDIAN BODY LINES

BACKGROUND

The present invention generally relates to managing human body pain, and more specifically, to using a meridian acupuncture sleeve to provide remote pain management through electrical stimulation of meridian body lines.

Known devices involve the application of an electrical impulse to selected acupuncture points to achieve a therapeutic result. These devices provide local stimulation to a variety of points around the body. However, these devices require direct application to many different points around the body to achieve their intended result. It would be desirable therefore to offer a device that consolidated application to a single area of the body while achieving whole body pain management. It would be further desirable to provide such consolidated application in a manner that makes the application of such therapy portable.

SUMMARY

Embodiments of the present invention are directed to using a meridian acupuncture sleeve to provide remote pain management through electrical stimulation of meridian body lines. A non-limiting example computer-implemented method includes loading, via a processor, a meridian tool into an electrical device having a touch screen. The computer-implemented method also includes causing, via the processor, the meridian tool to display a full human body image on the touch screen and receiving, via the processor, input signals on the touch screen to indicate pain points on the full human body image. The computer-implemented method further includes displaying, via the processor, a pain level screen on the touch screen and receiving, via the processor, pain level input on the pain level screen. The computer-implemented method finally includes causing, via the processor, the electrical device to provide controlling electrical pulses to a meridian acupuncture sleeve, wherein the controlling electrical pulses control the application of current being applied to electrical pads within the meridian acupuncture sleeve to provide pain relief for the pain points on the human body.

Other embodiments of the present invention implement features of the above-described method in a system and a meridian acupuncture tool.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIG. 3A illustrates another posterior view of a meridian acupuncture sleeve in accordance with one or more embodiments of the present invention;

FIG. 3B illustrates a side view of a meridian acupuncture sleeve in accordance with one or more embodiments of the present invention;

The diagrams depicted herein are illustrative. There can be many variations to the diagrams, or the operations described therein without departing from the spirit of the invention. For instance, the actions can be performed in a differing order or actions can be added, deleted or modified. Also, the term "coupled", and variations thereof describes having a communications path between two elements and does not imply a direct connection between the elements with no intervening elements/connections between them. All of these variations are considered a part of the specification.

DETAILED DESCRIPTION

One or more embodiments of the present invention takes advantage of a neurological system of reflexes to achieve pain relief and therapy via distal stimulation of known acupuncture points or zones. It is this distal application that, allows the entire body to be treated from the wrist, and that accounts for the profound therapeutic effect far superior to the massage like impact of local electrical stimulation of acupuncture points.

Although the word "acupuncture" is applicable to describing the goals and methods of the present invention, the present invention uses a style of acupuncture known as Balance Method Acupuncture or Distal Needle Acupuncture (DNA).

One or more embodiments of the present invention applies electrical stimulation to the wrist to stimulate acupuncture points, in addition to stimulating a combination of many points over six different meridian lines (Large Intestine, Small Intestine, San Jiao, Heart, Pericardium and Lung) to achieve an analgesic and therapeutic pain relief on target areas throughout the body. Embodiments of the present invention automate to a large extent the practice of acupuncture and can be applied to a variety of conditions.

One or more embodiments of the present invention address one or more of the above-described shortcomings of the prior art by providing a meridian acupuncture sleeve being remotely controlled by an external electronic device, such as a mobile phone. The electronic device supplies controlling electrical pulses to the meridian acupuncture sleeve which in turns provides electrical stimulation to the meridian body lines to control body pain throughout the body.

Figure 1:
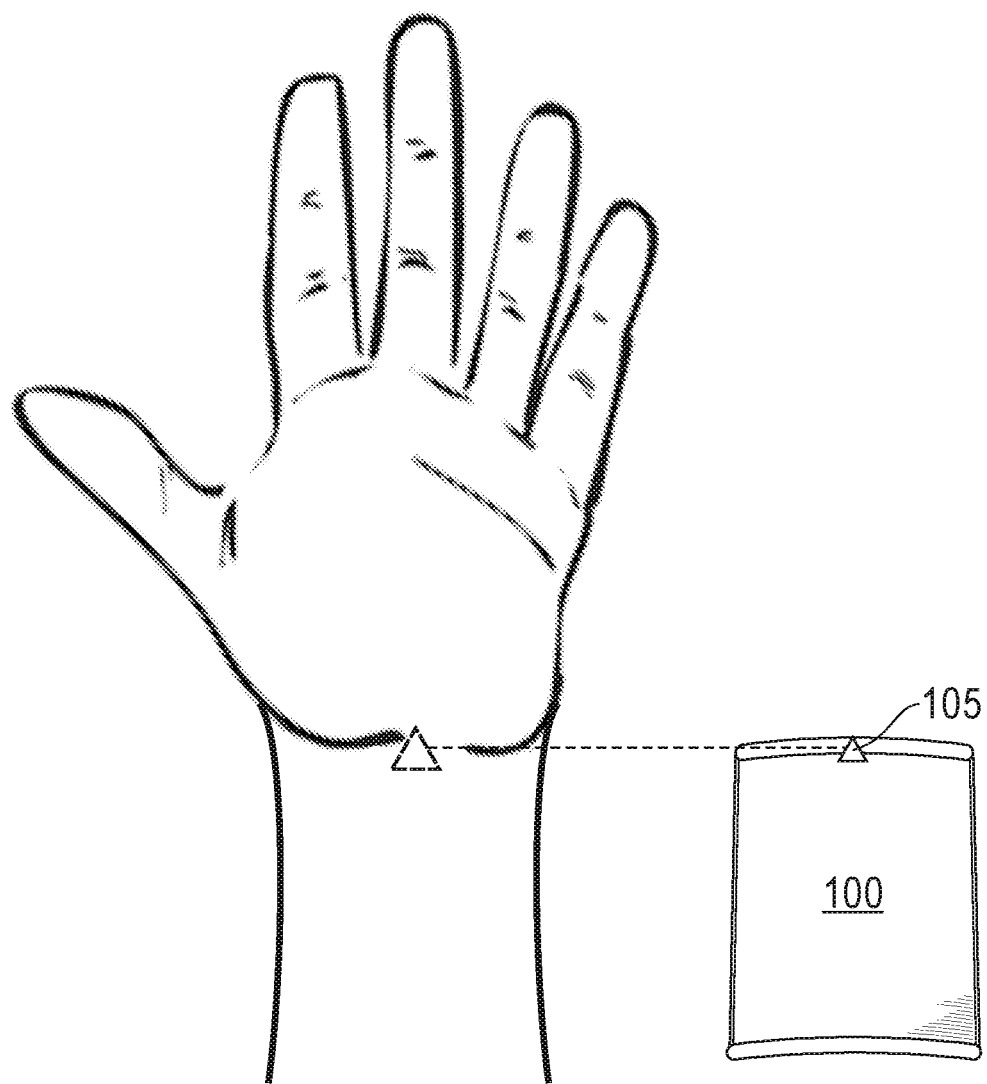
FIG. 1 illustrates an anterior view of a stimulation tool in accordance with one or more embodiments of the present invention.

Turning now to FIG. 1, shown is an anterior view of a stimulation tool in accordance with one or more embodiments of the present invention. The meridian acupuncture sleeve 100 shown in FIG. 1 includes an alignment point 105. The meridian acupuncture sleeve 100 is placed over the wrist and while viewing the anterior position of the wrist, the alignment point 105 is positioned at point A. Point A is the midline point at the distal wrist areas and indicated by a dotted line triangle on the wrist shown in FIG. 1. The sleeve 100 may be made from an elastic material that allows for it to be slip over the hand and slide into position on the wrist. The sleeve 100 allows for electric pads, described hereafter, to maintain adequate contact with the wrist of the wearer.

Figure 2A:
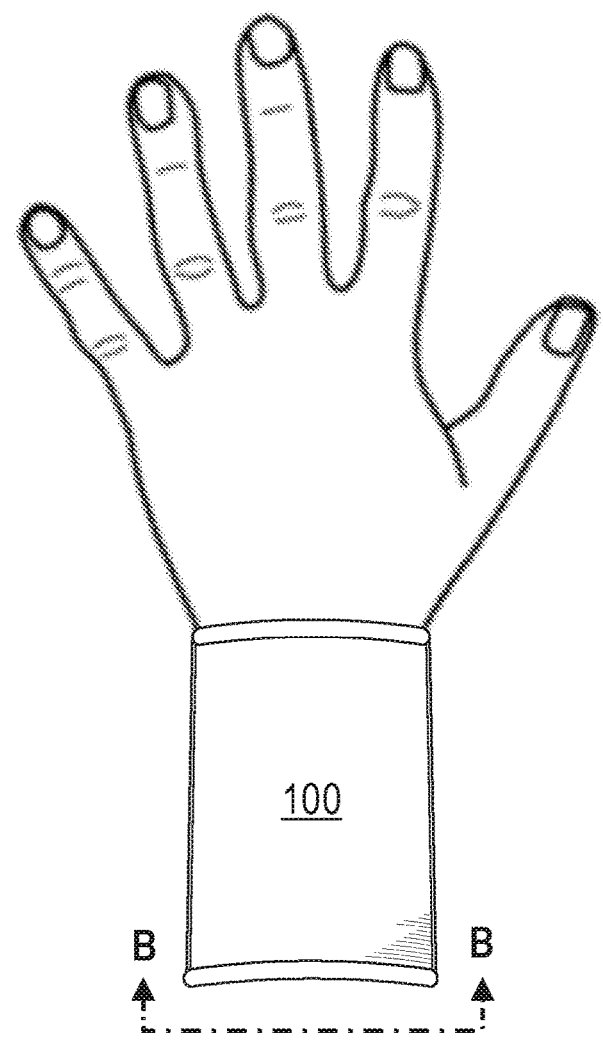
FIG. 2A illustrates a posterior view of a stimulation tool in accordance with one or more embodiments of the present invention.
Figure 2B:
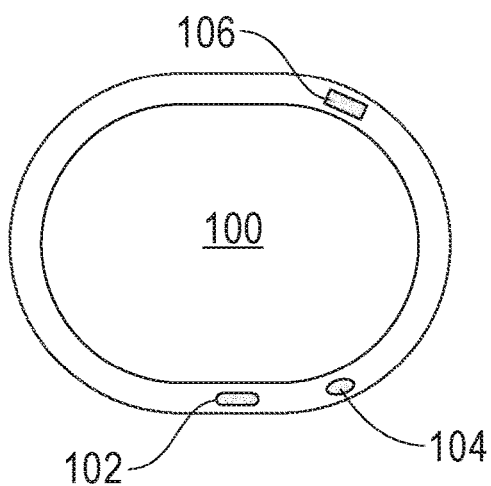
FIG. 2B illustrates a proximal view of a meridian acupuncture sleeve in accordance with one or more embodiments of the present invention.

Turning to FIGS. 2A and 2B, a posterior and proximal view of a meridian acupuncture sleeve 100 in accordance with one or more embodiments of the present invention is shown. The meridian acupuncture sleeve 100 includes an USB connection 102, a power supply charging port 104 and a wireless transceiver 106. The meridian acupuncture sleeve 100 can be controlled by using either the wired USB connection 102 or any known wired connection protocol for connecting a mobile phone or other controlling device to an electrical apparatus or using the wireless transceiver 106 to provide electrical stimulation to acupuncture points to one of the six different meridian lines within the wrist. Additional explanation for the application of electrical stimulation is described hereafter.

Referring to FIGS. 3A and 3B, a posterior and side view of a meridian acupuncture sleeve 300 in accordance with one or more embodiments of the present invention is shown. In more particular FIG. 3B is the side view along the "B-B" line of FIG. 3A. The meridian acupuncture sleeve 300 includes a pair of fixed retaining clips 305 and an adjustable spring clip 307. The fixed retaining clips 305 and the adjustable spring clip 307 are positioned to allow for the removable attachment of an electronic device (not shown). The meridian acupuncture sleeve 300 receives controlling stimulation electrical signals from the electronic device to control the application of electrical stimulation to acupuncture points using one of the six different meridian lines within the wrist.

Figure 4:
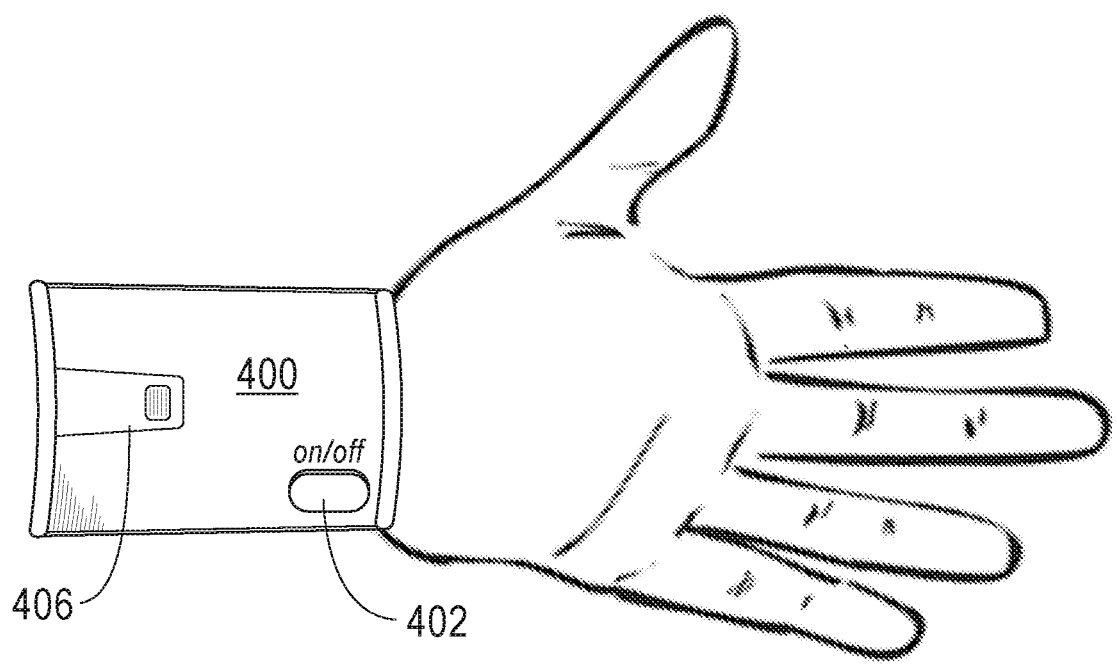
FIG. 4 illustrates another anterior view of a meridian acupuncture sleeve in accordance with one or more embodiments of the present invention.

Referring to FIG. 4, an anterior/Palmer view of a meridian acupuncture sleeve 400 in accordance with one or more embodiments of the present invention is shown. The meridian acupuncture sleeve 400 includes an on/off power button 402 and power supply 406. The meridian acupuncture sleeve 400 receives controlling stimulation electrical signals to apply the application of electrical stimulation by controlling the power supply 406 once the power button 402 is turned on. More details with regard to controlling the power supply 406 will be described herein below.

Figure 5:
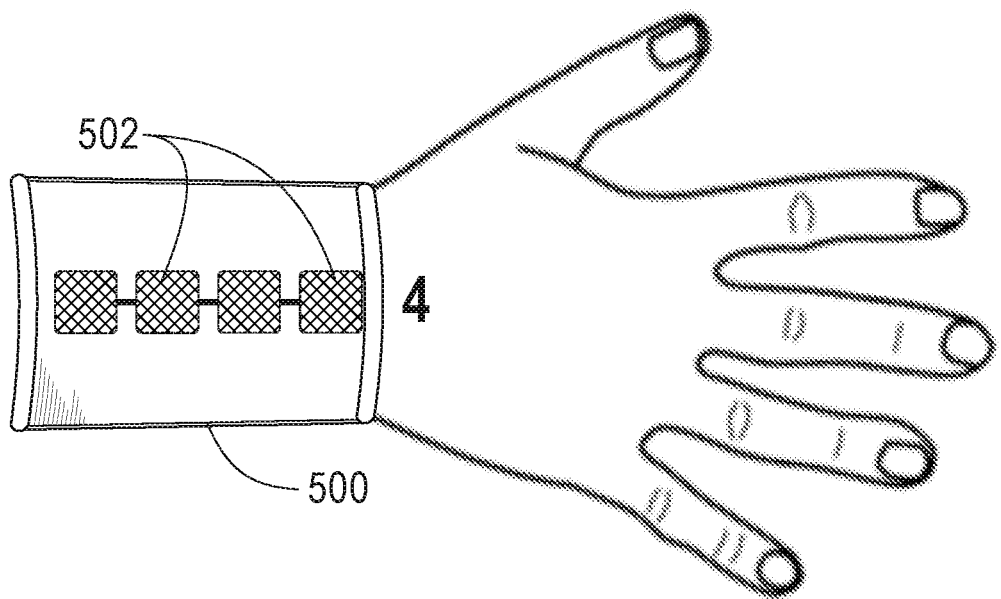
FIG. 5 illustrates a cut-away posterior view of a meridian acupuncture sleeve in accordance with one or more embodiments of the present invention.
Figure 6:
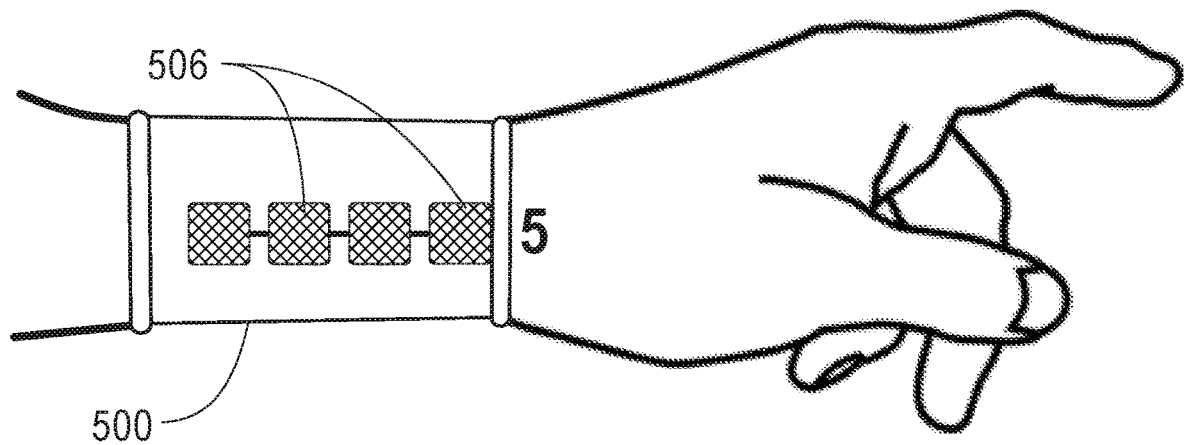
FIG. 6 illustrates a cut-away side lateral view of a meridian acupuncture sleeve in accordance with one or more embodiments of the present invention.
Figure 7:
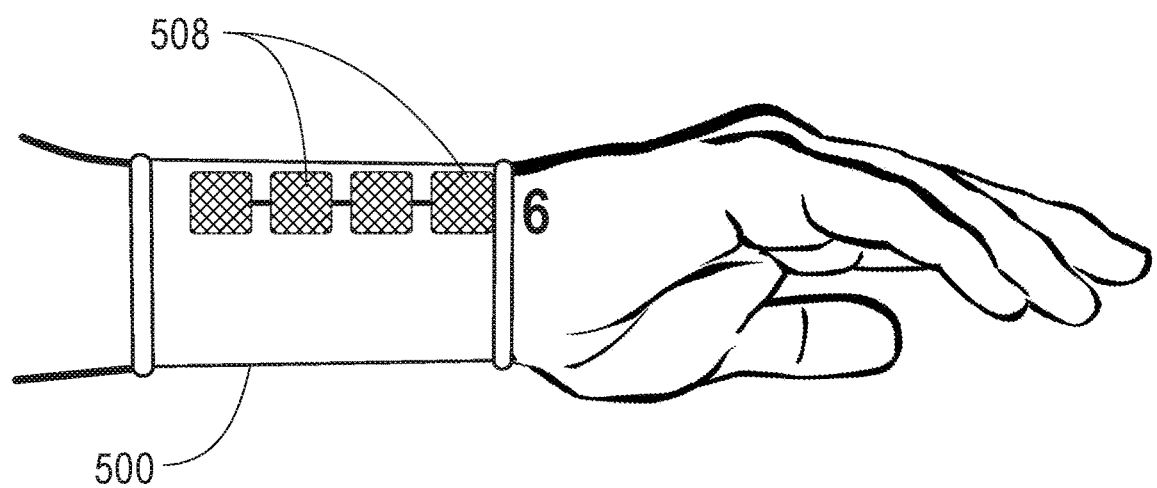
FIG. 7 illustrates a cut-away side medial view of a meridian acupuncture sleeve in accordance with one or more embodiments of the present invention.
Figure 8:
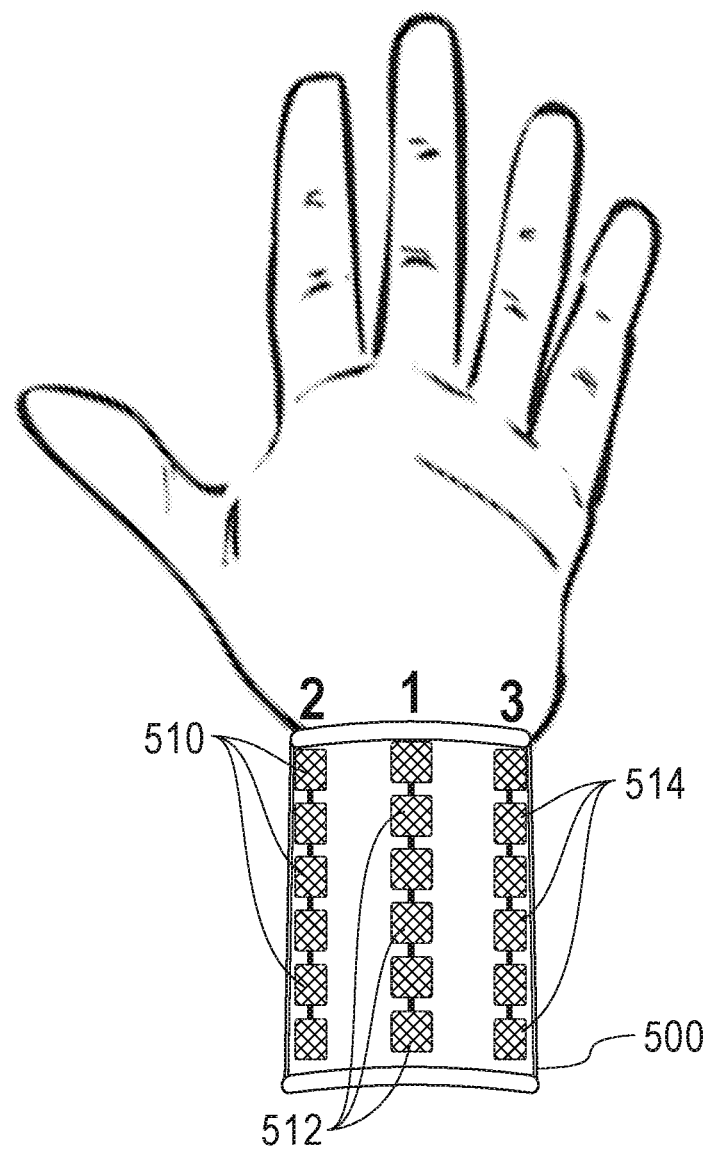
FIG. 8 illustrates a cut-away anterior view of a meridian acupuncture sleeve in accordance with one or more embodiments of the present invention.

Referring to FIGS. 5-8, shown are several cut away views of a meridian acupuncture sleeve 500 in accordance with one or more embodiments of the present invention is shown. The meridian acupuncture sleeve 500 includes electrical pads (502, 506, 508, 510, 512 and 514) along each of the meridian lines. Specifically, FIG. 5 shows a cut away posterior view of the meridian acupuncture sleeve 500 having electrical pads 502 along the San Jiao or Triple Burner meridian line 4. FIG. 6 shows a cut away side view of the meridian acupuncture sleeve 500 having electrical pads 506 along the Large Intestine meridian line 5. FIG. 7 shows a cut away side view of the meridian acupuncture sleeve 500 having electrical pads 508 along the Small Intestine meridian line 6. FIG. 8 shows a cut away anterior view of the meridian acupuncture sleeve 500 having electrical pads 512 along the Pericardium meridian line 1, electrical pads 510 along the Lung meridian line 2, and electrical pads 514 along the Heart meridian line 3. The meridian acupuncture sleeve 500 receives controlling stimulation electrical signals to apply the application of electrical stimulation by controlling a power supply once a power button is turned on. More detailed with regards to controlling the power supply will be described in more detail hereafter.

Figure 9A:
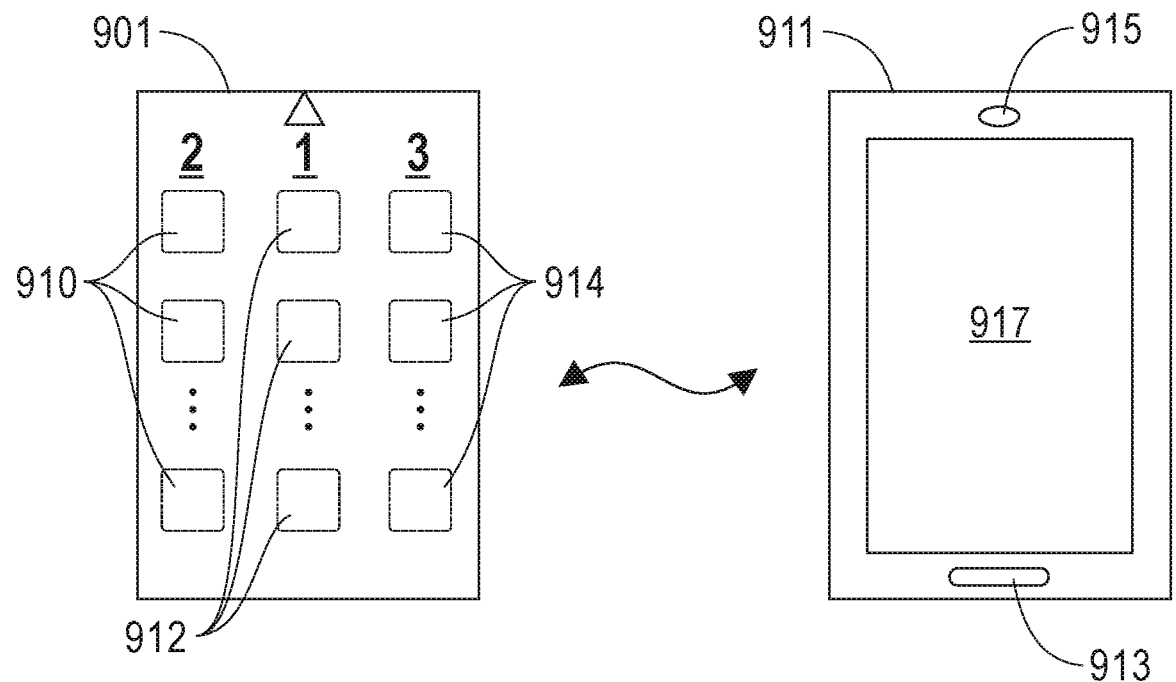
FIG. 9A illustrates an anterior view of a meridian acupuncture sleeve and a controlling electronic tool in accordance with one or more embodiments of the present invention.
Figure 9B:
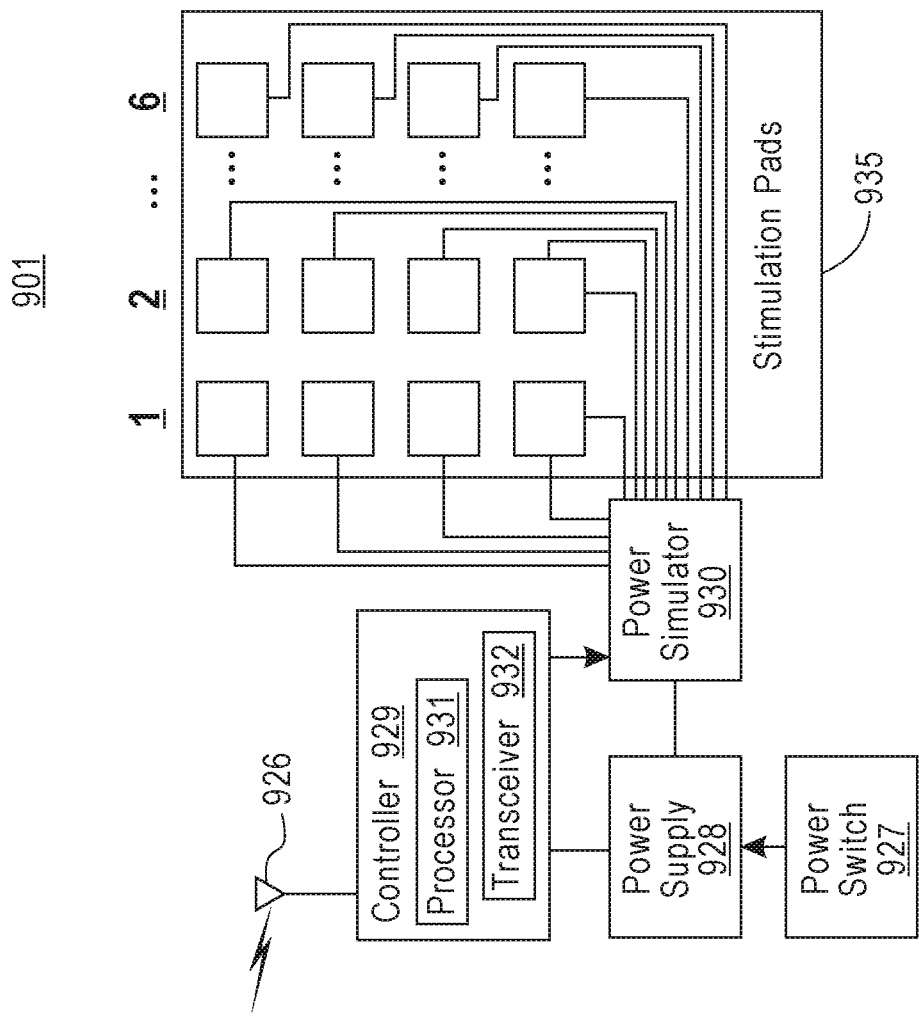
FIG. 9B illustrates a block diagram of a stimulation tool in accordance with one or more embodiments of the present invention.
Figure 9B:
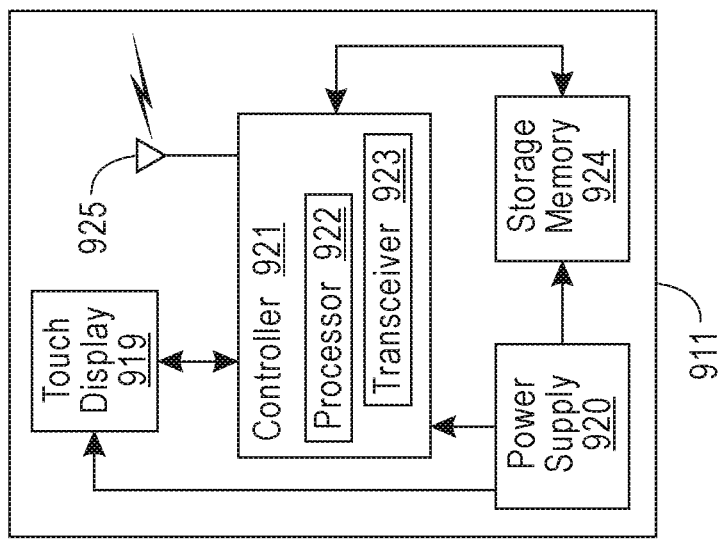

Referring to FIGS. 9A and 9B shown are a meridian acupuncture sleeve 901 being wirelessly controlled by an electronic device 911 in accordance with one or more embodiments of the present invention. With reference to FIG. 9A, an anterior view of meridian acupuncture sleeve 901 has embedded there in the electrical pads 912 along the Pericardium meridian line 1, electrical pads 910 along the Lung meridian line 2, and electrical pads 414 along the Heart meridian line 3. According to at least one embodiment of the present invention, the electronic device 911 is a mobile telephone having a microphone 913, a speaker 915 and a touch screen display 917.

Now referring to FIG. 9B, shown are electronic components of the meridian acupuncture sleeve 901 and the electronic device 911 in accordance with one or more embodiments of the present invention. The electronic device 911 includes a controller 921 having a processor 922 and transceiver 923. The electronic device 911 further includes a power supply 920, memory 924, a touch screen display 919 and an antenna 925. The electronic device 911 receives and runs a meridian acupuncture program for sending controlling stimulation electrical signals to the meridian acupuncture sleeve 901.

Still referring to FIG. 9B, the meridian acupuncture sleeve 901 includes a power supply 928 being controlled by a power switch 927. The meridian acupuncture sleeve 901 includes a controller 929 (having a processor 931 and a transceiver 932) and an antenna 926. The meridian acupuncture sleeve 901 includes a power switch 930 for supplying electrical stimulation to a plurality of electrical stimulation pads 935 which are aligned with meridian acupuncture lines (1-6) of the wrist. The controller 929 receives, via the antenna 926, the transmitted controlling stimulation electrical signals from the electronic device 911. Alternately, the controller 929 can receive instructions from a controlling device through a wired connection like that of the USB port 102. The controller 929 then controls the power switcher 930 based upon the received controlling stimulation electrical signals. The application of electrical stimulation by the power switcher 930 to the electrical stimulation pads 935 achieves the therapeutic equivalent of applying acupuncture to acupuncture points using one of the six different meridian lines within the wrist to relieve pain in the body. The electrical stimulation starts at the first distal pads and then as pain grows more proximal pads are activated.

There should be the ability to alter both the breadth and intensity of the electrical stimulations and additionally to recruit other meridians into the treatment. Another embodiment of the present invention would be three dials/controllers. 1. that spread the impulse further along the primary meridian being treated. 2. To increase the intensity of the meridian(s) being treated and 3. If more impact is needed then additional meridians can be recruited and those should have the ability to be affected by increasing the intensity and the spread along that meridian. Areas of pain can be treated with multiple meridians according to the relationships spelled out in Balance Method Acupuncture. Someone with Low Back Pain would start out being treated by the Lung meridian. They could then increase the intensity and/or the spread along that meridian for deeper impact. If that didn't result in satisfactory pain relief they could increase the "Depth" of the treatment and this "Depth" dial would recruit additional meridians according to these established relationships. So from Urinary Bladder it would then add in the Kidney meridian and then furthering this "Depth" could add in the Small Intestine Meridian and then the Heart and Large Intestine Meridians.

Figure 10:
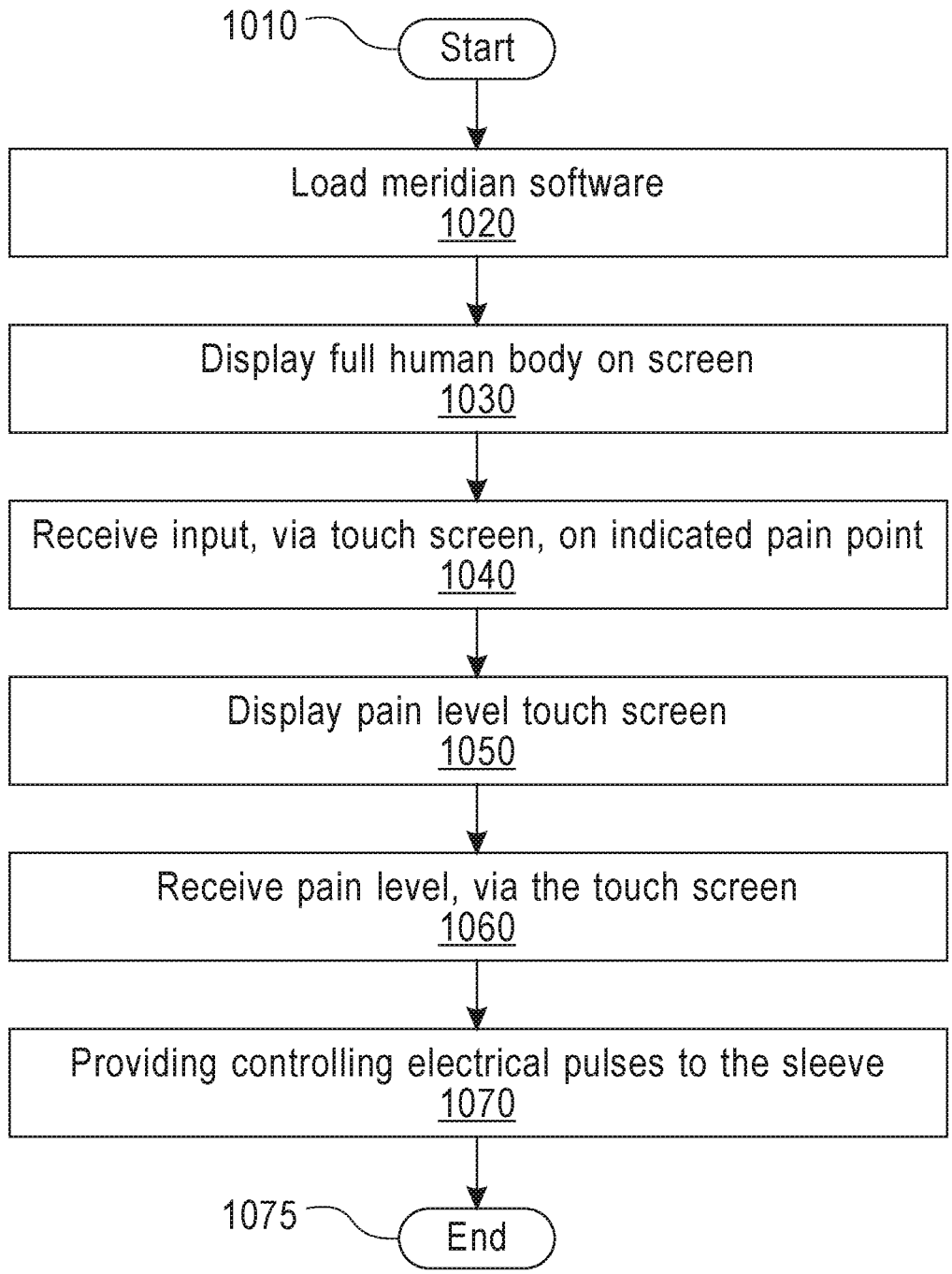
FIG. 10 illustrates a flow diagram of a process for a stimulation tool in accordance with one or more embodiments of the present invention.

Referring to FIG. 10, shown is a flow process for controlling a meridian acupuncture sleeve to provide remote pain management through electrical stimulation of meridian body lines in accordance with one or more embodiments of the present invention. The process starts 1010 by loading a meridian tool into an electronic device at block 1020. Once the meridian tool is loaded into the electronic device, the meridian tool displays a full body image on the electronic device at block 1030. The process receives input, for example, via a touch screen on the electronic tool, an indication of pain point at block 1040. Once a pain point has been identified, the process displays a pain level input screen at block 1050. The process receives the pain level, via the input screen, at block 1060. Once the pain level has been received, the process provides controlling stimulation electrical signals to a meridian acupuncture sleeve.

Figure 11:
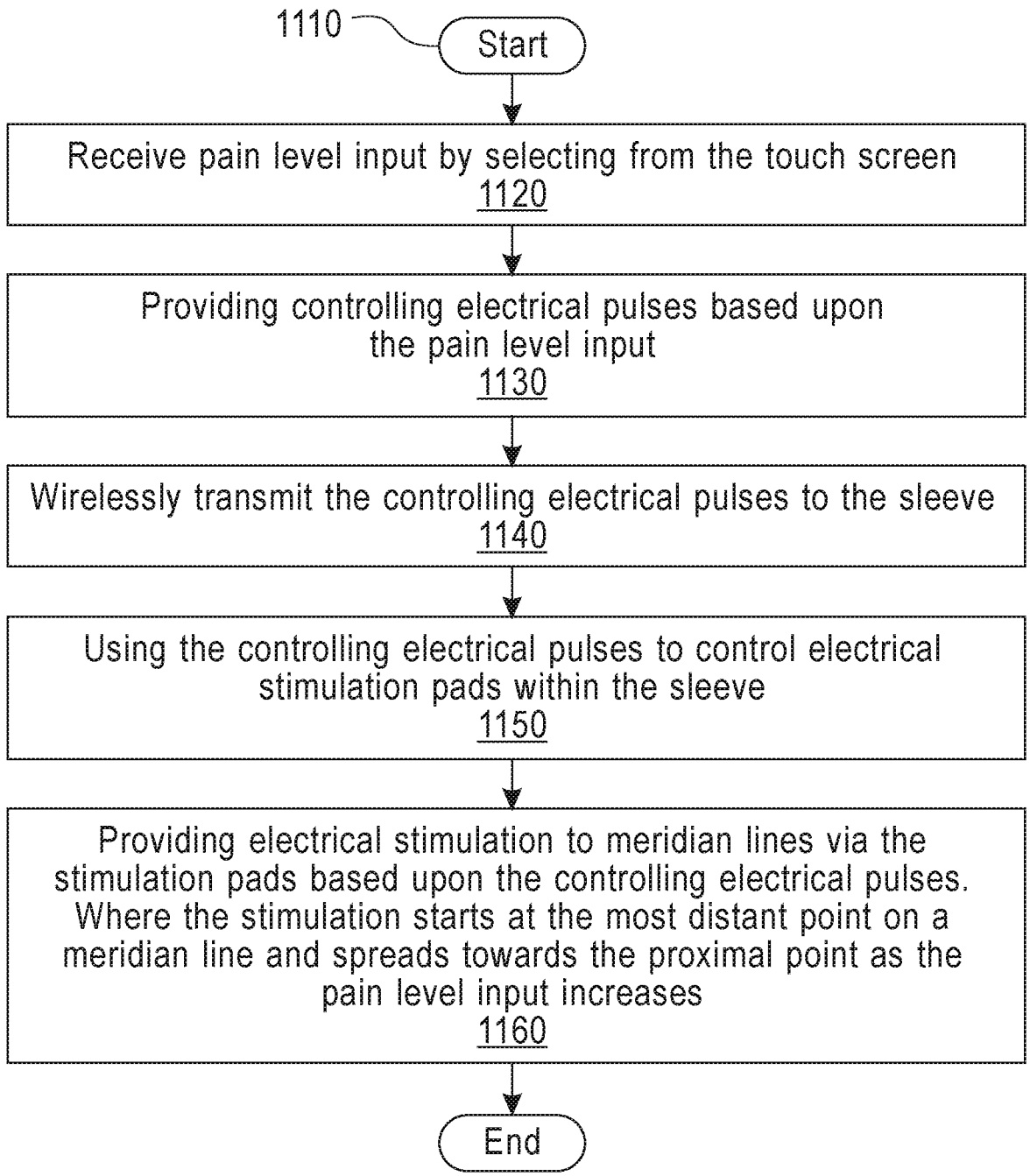
FIG. 11 illustrates another flow diagram of a process for a stimulation tool in accordance with one or more embodiments of the present invention.

Referring to FIG. 11, shown is another flow process for controlling a meridian acupuncture sleeve to provide remote pain management through electrical stimulation of meridian body lines in accordance with one or more embodiments of the present invention. The process starts 1110 by receiving pain level inputs on an input screen of an electronic device at block 1120. The process then provides controlling stimulating electrical pulses based upon the pain level input at block 1130. The controlling stimulating electrical pulses are wirelessly transmitted to a meridian acupuncture sleeve at block 1140. The process uses the received controlling stimulating electrical pulses to control electrical stimulation pads within the meridian acupuncture sleeve at block 1150. The process finishes by providing electrical stimulation to meridian lines, via the stimulation pads, based upon the controlling stimulating electrical pulses at block 1160. It is noted stimulation starts at the most distal point on meridian line and spreads towards the proximal point as the pain level input increases.

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

One or more of the methods described herein can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

In some embodiments, various functions or acts can take place at a given location and/or in connection with the operation of one or more apparatuses or systems. In some embodiments, a portion of a given function or act can be performed at a first device or location, and the remainder of the function or act can be performed at one or more additional devices or locations.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The present disclosure has been presented for purposes of illustration and description, but is not intended to be exhaustive or limited to the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The diagrams depicted herein are illustrative. There can be many variations to the diagram or the steps (or operations) described therein without departing from the spirit of the disclosure. For instance, the actions can be performed in a differing order or actions can be added, deleted or modified. Also, the term "coupled" describes having a signal path between two elements and does not imply a direct connection between the elements with no intervening elements/connections therebetween. All of these variations are considered a part of the present disclosure.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
   loading, via a processor, a meridian tool into an electrical device having a screen;
   causing, via the processor, the meridian tool to display a human body image on the screen;
   receiving, via the processor, input signals to indicate pain points throughout the human body image;
   displaying, via the processor, a pain level input display on the screen;
   receiving, via the processor, pain level input from the pain level input display screen; and
   causing, via the processor, the electrical device to provide controlling electrical pulses to a meridian acupuncture sleeve, wherein the controlling electrical pulses control the application of current being applied to electrical pads within the meridian acupuncture sleeve to provide pain relief for one or more indicated pain points throughout the human body, wherein the electrical pads provide electrical stimulation to a stimulation point on a meridian line on the human body, to provide the pain relief to the indicated pain remote from the stimulation point and wherein the pain relief is provided to the pain point by the stimulated meridian line; wherein the stimulated meridian line includes at least one known acupuncture point on the wrist the stimulation thereof achieving the therapeutic equivalent of applying acupuncture to the acupuncture point; and
   wherein the meridian acupuncture sleeve is removably worn on a wrist of the human body and the electrical pads within the meridian acupuncture sleeve are external to a dermis of the wrist.

2. The computer-implemented method of claim 1, wherein the electrical stimulation of the meridian line starts at the most distal point of the meridian acupuncture sleeve and spreads towards a proximal point as the pain level input increases, wherein an electrically stimulated region comprises the stimulation point.

3. The computer-implemented method of claim 1, wherein the electrical pads provide electrical stimulation to multiple meridian lines.

4. The computer-implemented method of claim 1, wherein the electrical device wirelessly provides the controlling electrical pulses to the meridian acupuncture sleeve.

5. The computer-implemented method of claim 1, wherein the electrical device is a mobile device.

6. The computer-implemented method of claim 1, wherein the electrical device is removably attachable to the meridian acupuncture sleeve.

7. A system comprising:
   a memory having computer readable instructions; and
   one or more processors for executing the computer readable instructions, the computer readable instructions controlling the one or more processors to perform operations comprising:
      loading a meridian tool into an electrical device having a touch screen;
      causing the meridian tool to display a full human body image on the touch screen;
      receiving input signals on the touch screen to indicate pain points throughout the full human body image;
      displaying a pain level screen on the touch screen;
      receiving pain level input on the pain level screen; and
      causing the electrical device to provide controlling electrical pulses to a meridian acupuncture sleeve, wherein the controlling electrical pulses controls the application of current being applied to electrical pads within the meridian acupuncture sleeve to provide pain relief for the indicated pain points throughout the human body, wherein the electrical pads provide electrical stimulation to a stimulation point on a meridian line on the human body, to provide the pain relief for the indicated pain remote from the stimulation point and wherein the pain relief is provided to the pain point by the stimulated meridian line; wherein the stimulated meridian line includes at least one known acupuncture point on the wrist the stimulation thereof achieving the therapeutic equivalent of applying acupuncture to the acupuncture point; and
      wherein the meridian acupuncture sleeve is removably worn on a wrist of the human body and the electrical pads within the meridian acupuncture sleeve are external to a dermis of the wrist.

8. The system of claim 7, wherein the electrical stimulation of the meridian line starts at the most distal point of the meridian acupuncture sleeve and spreads towards a proximal point as the pain level input increases, wherein an electrically stimulated region comprising the stimulation point.

9. The system of claim 7, wherein the electrical pads provide electrical stimulation to multiple meridian lines.

10. The system of claim 7, wherein the electrical device wirelessly provides the controlling electrical pulses to the meridian acupuncture sleeve.

11. The system of claim 7, wherein the electrical device is a mobile device.

12. The system of claim 7, wherein the electrical device is removably attachable to the meridian acupuncture sleeve.

13. A meridian acupuncture tool comprising:
a meridian acupuncture sleeve having one or more processors for executing computer readable instructions, the computer readable instructions controlling the one or more processors to perform operations comprising:
receiving signals to indicate pain points throughout a human body; and
controlling electrical pulses to electrical pads within the meridian acupuncture sleeve, wherein the controlling electrical pulses controls the application of current being applied to electrical pads to provide pain relief for the indicated pain points throughout the human body, wherein the electrical pads provide electrical stimulation to a stimulation point on a meridian line on the human body, to provide the pain relief to the indicated pain points remote from the stimulation point and wherein the pain relief is provided to the pain point by the stimulated meridian line; wherein the stimulated meridian line includes at least one known acupuncture point on the wrist the stimulation thereof achieving the therapeutic equivalent of applying acupuncture to the acupuncture point; and
wherein the meridian acupuncture sleeve is removably worn on a wrist of the human body and the electrical pads within the meridian acupuncture sleeve are external to a dermis of the wrist.

14. The meridian acupuncture tool of claim 13, wherein the electrical stimulation of the meridian line starts at the most distal point of the meridian acupuncture sleeve and spreads towards a proximal point of the meridian acupuncture sleeve as the pain level input increases, wherein an electrically stimulated region comprises the stimulation point.

15. The meridian acupuncture tool of claim 13, wherein the electrical pads provide electrical stimulation to multiple meridian lines.

16. The meridian acupuncture tool of claim 13, wherein the meridian acupuncture sleeve wirelessly receives the controlling electrical pulses.

17. The meridian acupuncture tool of claim 13, wherein the meridian acupuncture sleeve elastically slides over a hand of the human body.

* * * * *